United States Patent
Haefliger

(10) Patent No.: US 11,992,582 B2
(45) Date of Patent: May 28, 2024

(54) INTRAOCULAR LENS IMPLANT

(71) Applicant: ACCOMMO AG, Pfäffikon (CH)

(72) Inventor: Eduard Anton Haefliger, Pfäffikon (CH)

(73) Assignee: ACCOMMO AG, Pfäffikon (CH)

( * ) Notice: Subject to any disclaimer, the term of this patent is extended or adjusted under 35 U.S.C. 154(b) by 614 days.

(21) Appl. No.: 16/622,476

(22) PCT Filed: Jun. 15, 2018

(86) PCT No.: PCT/EP2018/065930
§ 371 (c)(1),
(2) Date: Dec. 13, 2019

(87) PCT Pub. No.: WO2018/229245
PCT Pub. Date: Dec. 20, 2018

(65) Prior Publication Data
US 2020/0206388 A1   Jul. 2, 2020

(30) Foreign Application Priority Data
Jun. 15, 2017  (EP) ..................... 17176165

(51) Int. Cl.
*A61L 27/54* (2006.01)
*A61F 2/16* (2006.01)
(Continued)

(52) U.S. Cl.
CPC ............ *A61L 27/54* (2013.01); *A61F 2/1613* (2013.01); *A61L 27/20* (2013.01); *A61L 27/3813* (2013.01);
(Continued)

(58) Field of Classification Search
CPC .. A61L 27/54; A61L 27/3813; A61L 27/3869; A61L 27/227; A61L 27/3666;
(Continued)

(56) References Cited

U.S. PATENT DOCUMENTS 4,296,501 A    10/1981  Kelman
4,608,050 A  *  8/1986  Wright ................. A61F 2/1616
                                                           128/898
(Continued)

FOREIGN PATENT DOCUMENTS

AU    2003301524 B2    5/2004
CN       202446299 U    9/2012
(Continued)

OTHER PUBLICATIONS

Shizuya Saika, et al., "Lens epithelial cell regeneration of a capsule-like structure during postoperative healing in rabbits", J Cataract Refract Surg—vol. 27, Jul. 2001.
(Continued)

*Primary Examiner* — Paul B Prebilic
(74) *Attorney, Agent, or Firm* — LADAS & PARRY LLP

(57) ABSTRACT

The invention concerns an intraocular lens implant for placement into an intracapsular space of a lens capsule of an eye and a composition, kit and methods related to the lens implant. The lens implant is designed for a placement into a posterior portion of the intracapsular space after removal of a native lens body and has a convex posterior surface. The lens implant is formed of one part and is manufactured from a suitable transparent non-structural cellular material. This keeps an anterior portion of the intracapsular space free of the implant which is dimensioned to comprise at most 40% of a volume of the native lens body.

17 Claims, 1 Drawing Sheet

(51) Int. Cl.
*A61L 27/20* (2006.01)
*A61L 27/38* (2006.01)
*A61L 27/22* (2006.01)
*A61L 27/36* (2006.01)
*C08L 5/08* (2006.01)

(52) U.S. Cl.
CPC ............. *A61L 27/3869* (2013.01); *A61F 2/16* (2013.01); *A61L 27/227* (2013.01); *A61L 27/3666* (2013.01); *A61L 2300/414* (2013.01); *A61L 2300/428* (2013.01); *A61L 2300/432* (2013.01); *A61L 2430/16* (2013.01); *C08L 5/08* (2013.01)

(58) Field of Classification Search
CPC ......... A61L 2300/414; A61L 2300/428; A61L 2430/16; A61F 2/16; A61F 2/1613; A61F 2250/0003; A61F 2250/0015; A61F 2250/0067; A61F 2250/0091
See application file for complete search history.

(56) References Cited

U.S. PATENT DOCUMENTS

| | | | |
|---|---|---|---|
| 4,834,753 A | 5/1989 | Sulc et al. | |
| 5,620,450 A * | 4/1997 | Eagles | A61F 2/167 606/107 |
| 5,627,162 A | 5/1997 | Gwon et al. | |
| 5,962,027 A * | 10/1999 | Hughes | A61F 2/14 623/6.63 |
| 6,450,642 B1 | 9/2002 | Jethmalani et al. | |
| 6,960,230 B2 | 11/2005 | Haefliger | |
| 8,447,086 B2 | 5/2013 | Hildebrand et al. | |
| 8,585,758 B2 | 11/2013 | Woods | |
| 2003/0187501 A1 | 10/2003 | Okada | |
| 2004/0054026 A1 | 3/2004 | Kunzler et al. | |
| 2005/0228401 A1 | 10/2005 | Zadno-Azizi et al. | |
| 2005/0246018 A1 * | 11/2005 | Grubbs | A61F 2/1635 623/6.37 |
| 2006/0216329 A1 | 9/2006 | Peyman | |
| 2007/0219633 A1 * | 9/2007 | Gwon | A61L 27/18 623/6.56 |
| 2010/0222879 A1 | 9/2010 | Bernard | |
| 2013/0053954 A1 | 2/2013 | Rao et al. | |
| 2013/0197636 A1 | 8/2013 | Haefliger | |
| 2015/0351901 A1 | 12/2015 | Stoy et al. | |
| 2016/0250020 A1 | 9/2016 | Kahook et al. | |
| 2020/0206388 A1 * | 7/2020 | Haefliger | A61F 2/1613 |

FOREIGN PATENT DOCUMENTS

| | | |
|---|---|---|
| EP | 2 185 575 A1 | 5/2010 |
| JP | 0323857 A | 1/1991 |
| JP | 2006516002 A | 6/2006 |
| WO | 2009/120908 A2 | 10/2009 |

OTHER PUBLICATIONS

Ehud I. Assia, et al., "Effect of expandable full-size intraocular lenses on lens centration and capsule opacification in rabbits", J Cataract Refract Surg—vol. 25, Mar. 1999.

J.J. Henry, "The Cellular and Molecular Bases of vertebrate Lens Regeneration", International review of cytology a survey of cell biology, vol. 228, p. 195-265, (published 2003).

Alexandre M. Rosen, et al., "In vitro dimensions and curvatures of human lenses", Elsevier, Vision Research 46 (2006) 1002 1009.

Shetal M. Raj, et al., "Post-Operative Capsular Opacification: A Review", International Journal of Biomedical Science, vol. 3, No. 04, Dec. 4, 2007.

P S Malik Krishnan, et al., "Nucleus management with Blumenthal technique: Anterior chamber maintainer", Indian J Ophthalmol, Jan.-Feb. 2009; 57(1): 23-25.

Goro Eguchi, et al., "Regenerative capacity in newts is not altered by repeated regeneration and ageing", Nature Communications, Accepted Jun. 13, 2011, Published Jul. 12, 2011, DOI: 10.1038/ncomms1389.

Jonathan J. Henry, et al., "Cell Signaling Pathways in Vertebrate Lens Regeneration. Published in 'New Perspectives in Regeneration' (E. Heber-Katz and D. L. Stocum, eds)", NIH Public Access, Published in final edited form as: Curr Top Microbiol Immunol. 2013 ; 367: 75-98. doi: 10.1007/82_2012_289.

Joshua Ford, et al., "Adjustable intraocular lens power technology", J Cataract Refract Surg—Jul. 2014; 40:1205-1223, 2014 ASCRS and ESCRS.

Haotian Lin, et al., "Lens regeneration using endogenous stem cells with gain of visual function", 2016 Macmillan Publishers Limited, Mar. 17, 2016, vol. 5 3 1, Nature, 3 2 3, doi:10.1038/nature17181.

Kai-Jing Zhou, et al., "In Vivo Observationof Lens Regeneratonin Rat Using Ulta-Long Scan Depth Opticla Choerence Tomography", In Vivo Observation of Lens Regeneration, Dec. 2016, vol. 57, No. 15, 6616.

Frank J. Lovicu, et al., "Fibrosis in the lens. Sprouty regulation of TGFβ-signaling prevents lens EMT leading to cataract", Published in final edited form as: Exp Eye Res. Jan. 2016; 142: 92-101. doi:10.1016/j.exer.2015.02.004.

Machine English translation of the CN202446299U, (Published Sep. 26, 2012).

ISR for International Application No. PCT/EP2018/065930, (Nov. 2018).

Written Opinion for International Application No. PCT/EP2018/065930, (Nov. 2018).

* cited by examiner

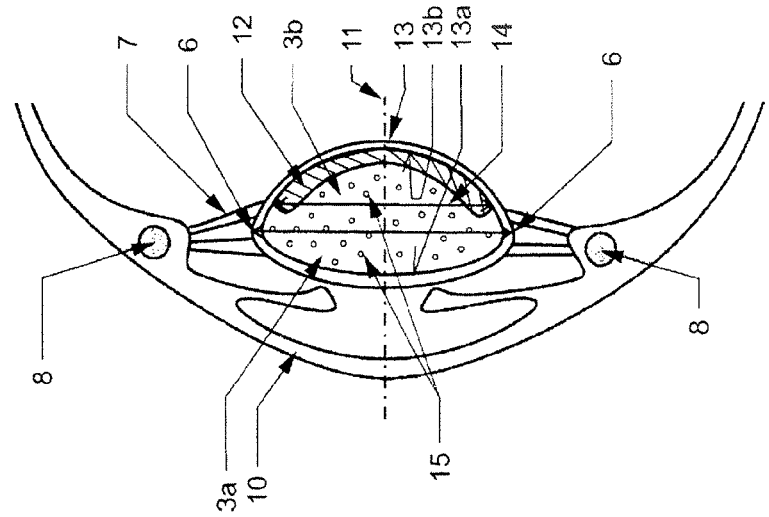
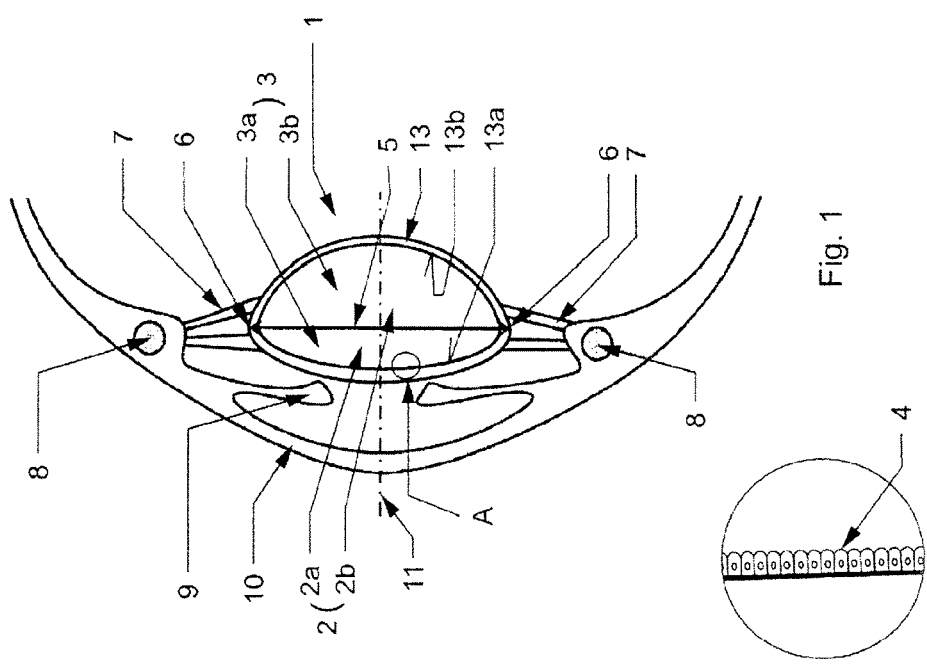

INTRAOCULAR LENS IMPLANT

RELATED APPLICATION

This application is an application under 35 U.S.C. 371 of International Application No. PCT/EP2018/065930 filed on 15 Jun. 2018, which claims priority of EP 17176165.3 filed 15 Jun. 2017 the entire contents of which are incorporated herein by reference.

BACKGROUND

The invention relates to the technical field human and veterinary medicine and in particular of ophthalmic surgery and concerns an intraocular lens implant for placement into a lens capsule and it furthermore concerns compositions, kits and methods related to the lens implant.

Intraocular lens implants for implantation into the lens capsule are known in the art. Removal of the native lens and replacement by an artificial intraocular lens is one of the most frequently performed surgical procedures in the world mainly for the treatment of cataract. Increasingly, this procedure is also envisioned for treatment of other lens defects such as age-related presbyopia. Generally, for lowering the risk of infections due to the surgery, care is taken to keep the opening of the eye and lens capsule through which the native lens body is removed and the artificial lens implant is introduced as small as possible.

A variety of commercially available lens implants accordingly are adapted to be introduced through small incisions into the capsular bag by being of a small size and/or by being made of artificial materials which are flexible such as silicone and acrylic materials. Usually such small lens implants comprise an optic zone and one or more haptic elements for fixing the implant to the capsular bag. Some accommodating lens implants available in the art connect a lens implant with haptic elements to the capsular bag such that it responds to the contraction and relaxation of the zonular apparatus of the eye for accommodation of the eye between near and distant vision. However, both the small size of such implants and the high refractive index of these flexible materials have caused an increased rate of dysphotopsias following cataract surgery with reflections of light on the retina disturbing vision in particular at night. A further common complication with intraocular implants is the formation of a secondary cataract.

In an alternative approach described in EP1251801, a full size lens implant was provided which corresponds in its size approximately to a physiological size of a lens body. It comprises two parts both made of artificially made materials for replacement of the lens body which when implanted axe juxtaposed to the anterior and posterior inner surface of the capsular bag. The posterior part of this two-part implant is made of a solid preferably flexible material facilitating its placement into the capsular bag. The anterior part of this two part implant is artificially made by e.g. synthetic material or by a material based on isolated natural preparations and includes e.g. polysiloxanes, hydrogels or collagen compounds which are introduced into the capsule preferably in a liquid state until the capsular bag is essentially filled and then cured in situ. The resulting two-part artificial lens implant thereby creates an intracapsular pressure like a natural lens body. The material in particular of the anterior part is selected to have similar elastic properties as a natural lens matter. Advantageously, this full size artificial lens is thereby designed to interact with the native accommodative system of the eye, i.e. with the zonulas and the ciliary muscle like a natural lens. A contraction of the ciliary muscle causes the zonulas to loosen and thereby causes in particular the anterior part of this two-part implant to assume a rounder shape. Thereby, as in a native lens, the increased curvature of the surface of the implant provides accommodation for near vision. Furthermore, it overcomes some of the disadvantages of smaller sized implants mentioned above.

However, this two-part full size lens implant still suffers from disadvantages which are also present in other types of lens implants capable of accommodation: It has been found that the lens capsule loses its elasticity within approximately 10 years after implantation of an artificially made implant with concomitant loss of the capability of accommodation for near vision.

DISCLOSURE OF THE INVENTION

Hence, it is a general object of the invention to provide an improved intraocular lens implant, in particular in combination with a capsular filling composition, for overcoming disadvantages of artificial lens implants available in the art.

In a first aspect, the invention provides an intraocular lens implant for a placement into a posterior portion of an intracapsular space after removal of a native lens body from a lens capsule of an eye. The lens implant is formed of one part and is manufactured from suitable non-cellular structural transparent material. The lens implant does not reach into an anterior portion of the intracapsular space, i.e. the anterior portion of the intracapsular space is kept free of non-cellular structural material or components thereof. The lens implant is devoid of any further part formed by non-cellular structural material or components thereof. The lens implant is dimensioned to comprise at most 40% of a volume of the native lens body. The lens implant has a convex posterior surface with a curvature which is shaped to fit a curvature of a posterior inner surface of the capsule.

The terms native lens or native lens body refer to the actual lens or lens body which was removed by surgery or they may refer to an average size of a physiological lens or lens body representative for a patient group such as e.g. adult human patients. The term lens body refers to the part of the lens which comprises the lens fibers.

A transparent shell called lens capsule (or capsule for short) surrounds the lens body. Removal of a the lens body comprising the lens fibers from the capsule results in an essentially empty capsular bag surrounding the intracapsular space. Such an empty capsule is essentially free from lens fibers, but it still comprises some or most of the lens epithelial cells lining the inner surface, in particular the inner anterior surface and also the inner surface in an equatorial area along the equatorial circumference of the capsule. Advantageously, gentle surgical procedures are available which leave most of the lens epithelial cells untouched (see below).

The lens implant according to the invention is manufactured from a suitable transparent non-cellular structural material. The degree of transparency may be selected according to the therapeutic use of the lens implant and may include partially transparent materials. The term non-cellular structural material refers to a structural material suitable for replacing removed lens fibers that does not comprise lens fiber cells or other biological cells. The non-cellular structural material is in particular a flexible material comprising manufactured inorganic or organic, artificial or natural structural material such as in particular polymeric material, e.g. polysiloxanes, hydrogels or collagens. It is in particular selected from a silicone, a hydrophobic acrylic material, a hydrophilic acrylic material, a hydrogel or a collagen polymer. The term subunit of the non-cellular structural material refers to components of the structural material such as e.g. monomers, dimers or oligomers of a polymer or polymer blend.

The lens implant according to the invention is formed of one part that replaces at most 40% of the native lens body, i.e. the lens implant fills the volume of the previously emptied capsular bag only up to at most 40%. In some embodiments the material composition of the one-part implant homogenous. In other embodiments the material composition may vary in different zones of the lens implant. It may differ e.g. in a central area around the visual axis from an equatorial area along the equatorial circumference. Since the lens implant is placed into the posterior portion of the capsular bag it keeps the anterior portion of the capsular bag free of non-cellular material. The lens implant is devoid of any further part. Reconstitution of the remaining volume of the lens body will occur after implantation of the lens implant by growth of cellular lens fibers.

Thus, the lens implant is an intracapsular implant, wherein the implant is complete by the one part of transparent structural material making up at most 40% of the volume of the removed native lens. This one part-lens implant is the sole deposit of non-cellular structural material inside the capsular bag. The lens implant is shaped to replace only a posterior portion of the lens body and to allow for the regeneration of an anterior portion of the lens body by lens fiber cells.

The term curvature of the posterior surface, (or posterior curvature for short), relates to the curvature of the posterior surface of the lens, or of the lens implant, either of which is juxtaposed to an inner posterior surface of the capsule. Evidently, radii of essentially identical or concentric circular bodies define these posterior surfaces. In particular, the term posterior curvature refers to the posterior curvature of the lens and lens capsule in a relaxed state of a ciliary muscle of the eye, i.e. in a state of the lens adapted to far vision. Notably, however, during accommodation the posterior curvature of the native lens does not change much, certainly not as much as an anterior curvature of the native lens does.

Furthermore, the natural curvature of the posterior surfaces of lens and capsular bag closely approximates the curvature of a sphere. The posterior radius of curvature of a physiological lens averages in a range of about 5.5 mm to 6 mm. The term shaped to fit a curvature of a posterior surface of the capsule therefore refers to an essentially spherical posterior surface with a radius of curvature ranging approximately from 5.5 mm to 6 mm plus or minus 25 percent, in particular plus or minus 20, 15, 10 or 5 percent. Thus, advantageously the posterior surface of the lens implant juxtaposed to the inner posterior surface of the empty capsule does not have to fit without any gap. The inventor observed that such a gap between an implant's posterior surface and the inner posterior surface of the capsule is filled following implantation by remaining lens epithelial cells. Because in response to a reduced intracapsular pressure these epithelial cells proliferate, grow and differentiate according to their physiological pathway to form one, several or many layers of transparent epithelial and/or lens fiber cells until a physiological intracapsular pressure is reached. The observed thickness of newly formed tissue filling the gap ranged from 1 µm to 1 mm, generally up to 100 µm or up to a few hundred µm such as up to 200, 300 or 400 µm. This type of controlled tissue growth was only observed after implantation of suitable implants under circumstances which postoperatively still provide for an intracapsular pressure which may be reduced, but is preferably reduced by less than a factor of two compared to a physiological intracapsular pressure. In contrast, if postoperatively there is essentially no intracapsular pressure present, remaining lens epithelial cells often engage in abnormal cell growth resulting e.g. in the formation of fibers and pearls and secondary cataract (posterior capsular opacification).

In some embodiments, the maximal length of the radius of curvature of the posterior surface of the lens implant juxtaposed to the inner posterior surface of the empty capsule is larger than the length of the posterior radius of curvature of the native lens body. The flexibility and elasticity of the capsular bag is able to compensate an increase in length of up to 25 percent, in particular up to 20, 15, 10 or 5 percent compared to the length of the posterior radius of curvature corresponding to the native lens.

In some embodiments, the posterior radius of curvature may be adapted according to measurements of the native lens body prior to its removal as obtainable e.g. by optical coherence tomography. The posterior surface of the lens implant may be shaped to fit the measured surface of a removed lens body within a tolerance of e.g. up to 10 µm or up to 100 µm, 300 µm or 1 mm, or in particular of around 100 µm plus or minus 25 µm or 50 µm.

In a second aspect, the invention relates to a capsule filling composition for use in intraocular surgery for filling an intracapsular space after removal of a native lens body from a lens capsule of an eye and accompanying the introduction of a lens implant manufactured of a suitable transparent non-cellular structural material as described above. The lens implant which is placed into the posterior portion of the intracapsular space only partially replaces the volume of the native lens body, at most up to 40%. The volume of the filling composition introduced into the capsule is adjusted such that together with the volume of the implant it provides for filling the capsule up to a volume which essentially reconstitutes the volume of the native lens body which was removed or of a lens body of an appropriate average size. The capsule filling composition is of an aqueous composition and is devoid of a non-cellular structural material which itself serves for the structural replacement of the lens fibers of the native lens body (2). The filling composition also does not comprise subunits of such materials, and in particular not subunits in amounts useful for formation of polymers as replacement of native lens fibers e.g. by in vivo curing as described in EP1251801.

However, the filling composition may comprise living cells for regenerative replacement of lens fibers originally present in the native lens body. Alternatively or additionally, it may comprise biochemical ingredients, in particular ingredients described below which promote regeneration of lens fibers by living cells e.g. ingredients which stimulate the proliferation and/or differentiation of living cells and in particular of lens epithelial cells.

Thus, in contrast to conventional implants, the implant and the filling composition according to the invention keep the anterior portion of the intracapsular space and in particular the anterior inner surface of the lens capsule with the lens epithelial cells untouched by non-cellular material and artificially made structural components. This is significant because the lens epithelial cells lining the inner anterior surface of the capsule are secreting the basement membrane constituting the anterior lens capsule during the entire life time. This keeps the anterior capsule flexible over a long time. In fact, the lens capsule generally is flexible up to an age of around 80 years in individuals without a lens implant, whereas in contrast after the implantation of a conventional lens implant already after about 10 years the capsules flexibility deteriorates often to the point of impairing or destroying the ability of accommodation.

Thus, advantageously, the implant according to the invention, the capsular filling composition according to the invention and the kit comprising both of them keep the anterior portion of the intracapsular space free of introduced artificial lens implant material and non-cellular structural components which may interfere with the lens epithelium cells' production of the basement membrane and thereby compromise the flexibility of the capsule and the capability of accommodation.

Furthermore, the filling composition advantageously provides for a replacement of the volume required for building up an intracapsular pressure, which essentially corresponds to the physiological intracapsular pressure prior to the removal of the native lens body. The filling composition as a physiological aqueous composition such as physiological saline optionally comprising suitable further ingredients known in the art allows or promotes the biological production of lens fibers by endogenous lens epithelial cells remaining on the inner surface of the capsule and/or by cells, in particular lens epithelial cells which are introduced into the intracapsular space along with or comprised in the filling composition. Recent work by Lin et al. (Nature, 531, p. 323, 2016), Lovicu et al. (Exp Eye Res, 142: p. 92, 2016) and others has demonstrated that lens epithelial cells are able to multiply and differentiate into lens fiber cells both in vitro and in vivo, demonstrating their ability to reconstitute a clear lens body or a portion thereof. Furthermore, the filling composition may advantageously facilitate the implant's remaining in a position in the posterior portion of the intracapsular space.

During an initial period after surgery while lens fibers are regenerating and gradually replacing the native lens body as far as it is not replaced by the implant, the accommodative capacity of a treated eye is gradually recovering with time. Advantageously, independent of the state of this regeneration, some degree of distant vision is possible already within a few hours after surgery due to the refractive power of the lens implant placed into the posterior portion of the capsule.

In a third aspect of the invention, the lens implant described above and the capsule filling composition described above are combined in a kit. The capsule filling composition of the kit advantageously provides for filling the volume of the intracapsular space and promoting cellular lens fiber growth after removal of the native lens body while leaving the anterior portion of the intracapsular space free of non-cellular material. This kit overcomes disadvantages of prior art implants as described above. In particular, the physiological cellular replacement of the native lens in the anterior intracapsular space provides for sustained elasticity of the anterior capsule required for accommodation.

A further advantage of the lens implant and filling composition according to the invention as mentioned above, is a reduction in the rate of formation of a posterior capsule opacification (secondary cataract) by uncontrolled growth of cells remaining in the capsule. However, in the event that a posterior capsule opacification nevertheless does occur, the placement of the implant according to the invention juxtaposed to the inner posterior surface of the lens capsule permits a particularly effective treatment: Areas of the posterior capsule that have thickened and turned opaque may be fully removed, by laser surgery such as e.g. by posterior capsulotomy using e.g. a Yag or a Femto laser across the entire thickness of the posterior capsule without creating a hole in the shell surrounding the intracapsular space. Thereby the implant enables full removal of opacified areas of the capsule in a wider range of cases.

A further aspect of the invention relates to a method of providing a personalized intraocular lens implant or a kit as described above for replacement of a native lens body. In some embodiments, the method comprises a step (a) providing of results of measurements regarding dimensions and/or optical power of an eye and/or comprises measuring dimensions and/or optical power of an eye. Such results or measurements concern in particular e.g. the optical power of the cornea or the native lens, the dimensions of the cornea or the lens, the length of the eye along the visual axis or the curvature of the posterior surface of the lens or lens capsule, etc. Furthermore, the method of providing a personalized kit or implant comprises a step (b) of selecting an implant as described above which is adapted regarding the provided or measured results of step (a).

A further aspect of the invention relates to a method of medical treatment of a patient comprising surgical removal of a native lens body and replacing it with an implant as described above and a capsule filling composition as described above, in particular for a treatment of cataract or presbyopia.

BRIEF DESCRIPTION OF THE DRAWINGS

The invention will be better understood and objects other than those set forth above will become apparent when consideration is given to the following detailed description thereof. This description makes reference to the annexed drawings, wherein:

FIG. 1 shows a sectional view of a healthy human eye depicting schematically parts relevant in the context of this invention.

FIG. 1A is an enlarged view of the encircled part of FIG. 1 identified by the letter "A".

FIG. 2 shows a schematic sectional view of a human eye after use of an exemplary embodiment of a kit comprising an exemplary embodiment of an intraocular lens implant and of an exemplary embodiment of a capsule filling composition for introduction into an intracapsular space after removal of a native lens body from a lens capsule.

MODES FOR CARRYING OUT THE INVENTION

The parts of the eye which are most relevant in the context of this invention are depicted schematically in a section of the eye in FIG. 1 with a lens 1, and an equatorial diameter 5 between two equatorial poles 6 of the lens 1, which equatorial diameter 5 divides the lens 1 into an anterior and a posterior portion. The term anterior refers to the side towards the cornea; the term posterior refers to the side towards the retina of the eye. The lens 1 comprises a lens body 2 divided accordingly along the equatorial diameter 5 into an anterior portion 2a and a posterior portion 2b.

The lens body 2 is essentially made up by transparent lens fibers. The lens body 2 is surrounded by a capsule 13 with anterior and posterior inner surfaces 13a and 13b. After removal of the lens body 2 an essentially empty capsule (or empty capsular bag) forms an intracapsular space 3. The intracapsular space 3 is divided along the equatorial diameter 5 into an anterior portion 3a and a posterior portion 3b. The equatorial diameter 5 is the largest diameter of the lens 2 or the capsule 13 or the intracapsular space 3, respectively and is oriented essentially perpendicular to the visual axis.

The capsule 13 is composed of an extracellular basement membrane comprising type IV collagen fibers and sulfated glycosaminoglycans. The capsule is elastic due to lamellar arrangement of collagen fibers. The capsule 13 is secreted anteriorly by lens epithelial cells 4 and posteriorly by elongating lens fiber cells. The lens epithelial cells (LECs) 4 line the anterior inner surface 13a of the lens capsule 13 as displayed enlarged in FIG. 1A. LECs 4 have been observed to additionally line an area of the inner capsular surface centering around the equator and reaching also into the posterior portion of the capsule. The LECs 4 not only secret the anterior portion of the lens capsule 13, they also differentiate into elongating lens fiber cells in an equatorial area along the equatorial circumference of the lens 1. Furthermore, the LECs are able to multiply and differentiate into lens fiber cells not only in vivo but also in vitro and they are able reconstitute a clear lens body 2 or a portion thereof In cataract surgery minimally invasive surgical techniques for removal of a defective lens have been developed. In a frequently applied method called capsulorhexis an incision in the capsule 13, in particular in the anterior part of the capsule 13, creates a circular opening which allows the lens body 2 to be extracted. In a commonly used procedure called phacoemulsification, the defective lens body 2 is emulsified by sonication and aspirated. Such surgical procedures as described e.g. by Zhou et al (Invest Ophthalmol Vis Sci. 2016; 57, p. 6615, see in particular also Supplementary 2) result in an essentially empty capsular bag surrounding the intracapsular space 3 with the anterior portion 3a and the posterior portion 3b from which the native lens body 2 has been removed. Advantageously, with such minimal invasive surgery most of the lens capsule 13 and the lining of LECs 4 on the anterior inner capsular surface 13a are left intact. It has been shown that this is permitting spontaneous regeneration of clear lens tissue (see e.g. Lin et al, 2016 cited above, extended data FIG. 1 or Zhou et al. Invest Ophthalmol Vis Sci. 2016, 57, p. 6615, Supplementary 2). In the method of medical treatment according to the invention including surgical removal of a native lens body, particular care is taken to place the incision into the capsular bag in a peripheral area of the lens capsule away from the visual axis 11. Furthermore, care is taken to keep the size of the incision small, in particular to keep a largest diameter of the incised hole below 3 mm, in particular below 2.5 mm, 2 mm, 1.5 mm or 1 mm. After introduction of the implant the incision is closed e.g. by a fibrin sealant or another a biological glue. Alternative options for closing the incision include e.g. laser tissue welding, introduction of a plug formed by a turnable lamella closure or introduction of a plug formed by a small amount of a curable artificial material (wherein no more artificial material is used than what is necessary for formation of a plug that closes the incision). Optionally, in some embodiments of the kit components for the closing of the incision into the capsular bag may be included.

FIG. 1 further shows the visual axis 11 perpendicular to the equatorial diameter 5 passing horizontally through cornea 10, iris 9 and lens 1. In FIG. 1 the eye is represented in a state adapted to distant vision as schematically shown by zonulas 7 attaching at the lens 1 circumferentially along the equator, as shown in FIG. 1 at both equatorial poles 6. The zonulas 7 are shown in a stretched state thereby flattening the lens 1. A circular ciliary muscle 8 upon contraction causes the zonulas 7 to relax which in turn permits the lens 1 to assume a rounder shape resulting in a higher refractive power and thereby accommodating the eye to near vision.

The radius of curvature of the posterior surface of the lens of an adult human eye ranges between approximately 4.5 and 7.5 mm with the radius of posterior curvature averaging around 5.5 to 6 mm in a human adult eye. The equatorial diameter of the lens of an adult human eye ranges between approximately 9 to 11 mm. The volume of the lens of an adult human eye as measured in vitro ranges from approx. 180 µl to 280 µl (Rosen et al, Vision Research 2006, 46: 1002). The volume of the lens 1 of an adult human eye essentially corresponds to the volume of the lens body 2 and to the volume of the intracapsular space.

FIG. 2 shows an exemplary embodiment of an intraocular lens implant 12 placed into the posterior portion 3b of the intracapsular space 3. As evident from this exemplary embodiment, the lens implant 12, made of a suitable transparent material does not reach into the anterior portion 3a of the intracapsular space 3. The volume of the lens implant 12 is less than 40% of the volume of the native lens body 2; in exemplary embodiments it may be below 20% or 10% of the volume of the native lens.

In some embodiments, the lens implant 12 is dimensioned to comprise at most 35%, 30%, 25%, 20%, 15%, 10%, 5% or 2% of a volume of the native lens body 2. In in particular, the lens implant 12 is dimensioned to comprise a volume of at most 120 µl, 110 µl, 100 µl, 90 µl, 80 µl, 70 µl, 60 µl, 50 µl, 40 µl 30 µl, 20 µl or 10 µl.

The lens implant 12 is manufactured from a suitable transparent material, in particular selected from flexible materials, e.g. materials known in the art for the manufacture of intraocular lenses such as silicone or hydrophobic and hydrophilic acrylic materials, hydrogels or collagen polymers.

The lens implant 12 has a convex posterior surface with a curvature—or a posterior curvature for short—which is shaped to fit a curvature of a posterior surface of the capsule 13. In some embodiments of the lens implant 12, the radius of curvature of the posterior surface varies in a range of 4 to 8 mm, in particular in a range of 5.5 mm to 6 mm plus or minus up to 25 or 20 or 15 or 10 or 5 percent or e.g. in ranges of 4.6 to 7.5 mm or 5 to 7 mm or around 6 mm.

The above-indicated radii of curvature refer in particular to the radius of curvature measured on the visual axis 11 or in a vicinity of the visual axis 11. The vicinity of the visual axis is defined as a range adjacent to the visual axis within a solid angle of up to 10°, up to 20° or up to 30° of the visual axis 11.

In some of these and other embodiments, the lens implant 12 has a maximal diameter 14, in particular a maximal outer diameter 14 as measured from an outside surface to an outside surface of the lens implant 12, which at most equals the length of an equatorial diameter 5 of the native lens 1. The maximal diameter 14 in particular, as shown in FIG. 2, is perpendicular to the visual axis 11 of the eye and parallel to the equatorial diameter 5. In particular, the maximal diameter 14 of the implant 12 measures at most 98%, 95%, 90%, 80%, 70%, 60% or 50% of the equatorial diameter 5 of the native lens 1. In some of these and other embodiments the maximal diameter 14 of the implant 12 measures at least 50%, 60%, 70%, 80% or 90% of the equatorial diameter 5 of the native lens 1. In some embodiments, the maximal diameter 14 of the implant 12 measures in a range with an upper boundary of 5 to 12 mm, in particular 11, 10, 9, 8, 7, or 6 mm. In some of these and other embodiment of the implant the lower boundary of the maximal diameter 14 of the implant is in a range of 3 to 7 mm, in particular 3, 4, 5 or 6 mm. Embodiments of the lens implant with a maximal diameter 14 that is smaller than the equatorial diameter 5 of the native lens do not reach into an equatorial portion of the intracapsular space. Thereby epithelial cells lining an equatorial area of the inner surface also in a posterior portion of the capsular bag remain untouched by non-cellular structural material. The size of this untouched posterior equatorial portion increases with a decreasing maximal diameter 14 of the implant.

In some of these and other embodiments, the lens implant 12 is manufactured from a transparent material which is selected to be deformable, thereby allowing the implant 12 to be introduced into the intracapsular space 3 in a folded or rolled-up state through an opening in the lens capsule 13. In some embodiments, the lens implant is manufactured from flexible materials which allow the implant to be introduced through openings of the capsule 13 wherein the largest diameter of the opening measures in the range of 0.5 to 4 mm, in particular between 0.5 and 3 mm, more particularly less than 3, 2, 1.75, 1.5 or 1.25 or 1 mm.

In some of these and other embodiments, the lens implant 12 is manufactured from a transparent material which is expandable by absorption of liquid. In these embodiments the implant 12 when after introduction into an aqueous environment within the lens capsule it has reached its expanded volume, its properties including shape and size correspond to properties described here for embodiments of the implant which are not manufactured from an expandable material. Expandable lens materials are known in the art. e.g. the commercial y available implants (Acqua) made from hydrophilic acrylic polymers comprising hydroxyethyl methacrylate, vinyl pyrilidone and methylmethacrylate or a hydrophilic polymer or hydrophilic/hydrophobic copolymer such as described by Mehta in an article on the world-wide web at boamumbai.com/journalpdfs/jan-mar2001/torpedo or such as described in U.S. Pat. No. 4,834,753 or expandable hydrogels as described in WO2004/026928.

In some of these and other embodiments, the lens implant 12 has an anterior surface of the implant 12 which is also convex or it has an anterior surface which is plan or it has an anterior surface which is concave. In some embodiments, the lens implant has a posterior convex and an anterior concave side with a positive meniscus or a negative meniscus appropriately dimensioned for achieving a desired refractive (i.e. optical) power. In some embodiments the lens implant can be toric to correct for astigmatism.

In some embodiments, the lens implant 12 is dimensioned and shaped to provide a refractive power suitable for vision adapted to infinity, in particular with a refractive power in a range between of −20 dioptre to +60 dioptre, as desired for the treatment of a particular patient. Lens implants 12 with a refractive power of 0 are included, because the lens implant independently of an optical power correction due to its adaptation in shape to the posterior inner surface of the capsule 13b allows for particularly effective treatment of secondary cataract by laser surgery, whereby areas of the posterior lens capsule may be even fully removed and still keep the intracapsular space 3 enclosed by a shell without holes as described above.

Besides showing an exemplary embodiment of an intraocular lens implant 12 placed into the posterior portion 3b of the intracapsular space 3, FIG. 2 also schematically shows an exemplary embodiment of a capsule filling composition 15 for use in intraocular surgery and how this filling composition 15 may be filling the intracapsular space 3 within the lens capsule 13. Evidently, the filling composition 15 fills not only the anterior portion 3a of the intracapsular space 3 but also parts of the posterior portion 3b of the intracapsular space 3. It thereby essentially replaces the remaining volume of the removed native lens body 2 to the extent that it is not replaced by the lens implant 12. The volume of the filling composition 15 accordingly may be defined as a complementary volume to the volume of the implant 12, wherein the sum of the two corresponds to the volume of the native lens body 2, or intracapsular space 3 within the empty capsular bag.

The capsule filling composition 15 is of an aqueous composition and is devoid of non-cellular structural components for permanent replacement of lens fibers comprised by the native lens body. The capsule filling composition 15 by filling up the intracapsular space 3 provides for an intracapsular pressure, which corresponds to a physiological intracapsular pressure prior to the removal of the native lens body. An intact intracapsular pressure is relevant for the accommodative function of the eye.

The shape, geometry and size of the lens implant 12 is not restricted to the exemplary shape and size as depicted in FIG. 2, but may be quite freely adapted to fit the size and optical characteristics of a particular eye and to yield a desired refractive power, provided that the lens implant 12 does not reach into the anterior portion 3a of the intracapsular space 3 and in particular that the lining of epithelial cells 4 on the anterior inner surface 13a of the capsule 13 are not in contact with the implant 12, but instead with the capsular filling composition 15.

In some of these and other embodiments the capsule filling composition 15 comprises living cells. Such cells may be obtained e.g. from an in vitro culture or from a tissue probe. In particular, the cells may be obtained from a probe of an eye, more particularly from a probe comprising lens epithelial cells 4. In particular, the cells which are added to the aqueous filling composition 15 are capable of developing lens fibers and/or are secreting factors promoting the formation of lens fibers from remaining or added lens epithelial cells.

In some of these and other embodiments, the cells comprised by the capsule filling composition 15 are derived from autologous or heterologous human eyes or from non-human eyes, in particular from non-human mammalian eyes with or without in vitro culturing prior to the mixing of the cells into to the capsule filling composition or prior to administering the cells along with the capsule filling composition 15 into the intracapsular space 3. The transplantation of heterologous or non-human cells, benefits from the fact that the contents inside the capsule 13 are immune-privileged, i.e. not accessible to the immune system and therefore not prone to immune rejection. In some embodiments the capsular filling composition is administered as one fraction, in other embodiments it is administered in several fractions, wherein the fractions may be administered at the same time or at separate times and they may be of the same or of a variable composition.

In some of these and other embodiments of the capsule filling composition 15, it comprises ingredients in particular selected from:
  hyaluronic acid,
  a growth factor, in particular one or several of: a fibroblast growth factor, including FGF-1 and FGF-2, epidermal growth factor (EGF), platelet-derived growth factor (PDGF), insulin growth factor I or II (IGF-I or IGF-II),
  an anti-TGFβ blocking agent
  a retinoid The term ingredient refers to a liquid or soluble compound which is suitable for establishing a physiological aqueous environment in the lens capsule, and may be based e.g. on a physiological saline solution. The term ingredient includes in particular active ingredients with an active biochemical function such as e.g. ingredients which actively promote regeneration of clear lens fiber tissue. For example, Lovicu et al. (Exp Eye Res, 142: 92, 2016) have shown that anti-TGFβ blocking agents promote the initiation of lens fiber formation from lens epithelial cells. In addition, there are growth factors known which stimulate lens regeneration as reviewed e.g. by Henry (Int. Rev. Cytology, 228: 195, 2001). Further ingredients include nutrients, antibiotic agents or other agents with a biochemical effect, such as e.g. osmotically active ingredients modulating the intracapsular pressure.

In a further aspect, a kit comprising both a lens implant 12 and a capsule filling composition 15 as they are described above is provided. In some embodiments of the kit, a collection of implants of different sizes and/or shapes and/or refractive power may be included in the kit for selection of the appropriate implant according to a patients need. The kit is suitable for fully replacing the volume of a removed native lens body 2. In some embodiments of the kit, lens implants and samples with complementary volumes of a capsule filling composition resulting in essentially the same volume as the volume of the native lens body may be provided. The filling composition 15 may facilitate regeneration of lens fibers based on residual cells or based on added cells, in particular lens epithelial cells. In some embodiments, the filling composition may actively promote regeneration by comprising active ingredients, in particular selected ingredients according to the needs of a particular patient. In some embodiments the kit may comprise further suitable components to be used or to be administered to the eye a during, before or after surgery.

A further aspect concerns a method for providing a personalized intraocular lens implant 12 or for providing a personalized kit comprising an intraocular lens implant 12 as described above and optionally further comprising a capsule filling composition 15 as described above. In some embodiments of the method of providing the kit comprises steps (a) of measuring an eye and a step (b) of selecting at least one implant 12. In step (a) in particular the dimensions of the cornea and/or of the lens and/or the axial length eye are determined. The axial length of an eye or eyeball is defined by the distance between the anterior and the posterior poles of the eyeball. Step (a) and step (b) may be performed at different times and in particular prior to the operation such as e.g. several weeks before the operation, in particular up to 1 or 2 months before the operation. Such methods of measurements are possible without invasive or surgical procedure performed on a human or animal body. Further embodiments of the method of providing a personalized lens implant or kit in step (a) rely on the provision of measurement results obtained from an external source.

Methods of measuring an eye and the size of the lens capsule are known in the art (see e.g. WO 2011/02068). Biometric methods include ultrasound biometry such as for cataract and refractive treatment in recent years routinely used laser interference biometry (also called optical biometry) of the eye. An alternative method known in the art is partial coherence interferometry. Commonly used and commercially available exemplary ocular biometers include the IOL Master of Zeiss and the Lenstar system of Haag Streit.

In some embodiments of the method of providing the personalized kit in an additional step the ingredients of the filling composition 15 are adapted to the needs of a particular patient. In some embodiments the filling composition 15 is adapted e.g. by addition of autologous cells or by a selection of heterologous living cells and/or of a particular ingredient or active ingredient. In some embodiments of the method of providing a personalized kit with the filling composition comprising cells, the cells may be cultured in vitro e.g. for amplification according to procedures known in the art. The filling composition may be provided in the kit with all ingredients pre-mixed. Alternatively, the filling composition may be provided in a number of fractions some of which may comprise ingredients or cells to be added and mixed into the filling composition at a prescribed time before administration of the filling composition to the patient or to be administered into the intracapsular space along with the filling composition as a separate fraction of the filling composition at the same or at a different time.

In some embodiments of the method a preferable volume or a range of volumes of the filling composition complementary to the volume of the implant is determined for introduction into the intracapsular space.

By way of this method of providing a personalized kit comprising one or more implants 12 or in some embodiments by additionally comprising a filling composition 15, the implant or kit are advantageously adapted to the particular needs of a patient e.g. in a suitable time ahead of the surgical procedure.

While there are shown and described presently preferred embodiments of the invention, it is to be distinctly understood that the invention is not limited thereto but may be otherwise variously embodied and practiced within the scope of the following claims.

The invention claimed is:

1. A kit consisting of a lens implant for a placement into a posterior portion of an intracapsular space after removal of a native lens body from a lens capsule of an eye and a capsule filling composition for use in intraocular surgery for filling the intracapsular space after introduction of the lens implant wherein the lens implant is formed of one part and manufactured from a suitable transparent non-cellular structural material, wherein the non-cellular structural material is selected from the group consisting of: a silicone, a hydrophobic acrylic material, a hydrophilic acrylic material, a hydrogel, and a collagen polymer, wherein the lens implant is dimensioned to keep an anterior portion of the intracapsular space free of non-cellular structural material and subunits thereof, wherein the lens implant is devoid of any further part formed by the non-cellular structural material or subunits thereof, wherein the lens implant comprises at most 40% of a volume of the native lens body, which was removed or of the volume of a native lens body with an average size, and wherein the lens implant has a convex posterior surface with a curvature which is shaped to fit a posterior inner surface of the capsule, wherein the volume of the filling composition and the volume of the lens implant are such as provide for reconstitution of a volume essentially corresponding to the volume of the native lens body which was removed or of the volume of a native lens body with an average size and wherein the capsular filling composition is of an aqueous composition and is devoid of said non-cellular structural material or subunits thereof.

2. A method for providing a kit according to claim 1 consisting of the intraocular lens implant and the capsular filling composition for use in intraocular surgery after removal of a native lens body comprising the steps of a. providing results of measurements of an eye and b. selecting a lens implant based on the results of step a.

3. The method according to claim 2 wherein in an additional step, the ingredients of the filling composition include cells capable of developing lens fibers and derived from one of an autologous human eye or a heterologous human eye or a non-human mammalian eye or a non-human, non-mammalian eye and/or an ingredient, selected from the group consisting of:
hyaluronic acid,
an anti-TGFP blocking agent,
a growth factor selected from the group consisting of a fibroblast growth factor, epidermal growth factor (EGF), platelet-derived growth factor (PDGF), and insulin growth factor I or II (IGF-I or IGF-II), and
a retinoid.

4. The kit according to claim 1,
wherein the lens implant is dimensioned to comprise at most 35%, 30%, 25%, 20%, 15%, 10%, 5% or 2% of a volume of the native lens body.

5. The kit according to claim 1,
wherein a radius of curvature of the posterior surface of the lens implant is in a range of 4 to 8 mm.

6. The kit according to claim 1,
wherein a maximal diameter of the implant at most equals the length of an equatorial diameter of the native lens or
wherein a maximal diameter of the implant measures at most 98%, 95%, 90%, 80%, 70%, 60% or 50% of the equatorial diameter of the native lens.

7. The kit according to claim 6, wherein a maximal diameter of the implant measures at least 50%, 60%, 70%, 80% or 90% of the equatorial diameter of the native lens.

8. The kit according to claim 1,
wherein the transparent material of the lens implant is selected to be deformable, allowing the implant to be introduced into the intracapsular space in a folded or rolled-up state through an opening in the lens capsule, wherein the largest diameter of the opening measures in the range of 0.5 to 4 mm.

9. The kit according to claim 1,
wherein an anterior surface of the implant is also convex or wherein the anterior surface is planar or concave.

10. The kit according to claim 1,
wherein the lens implant is dimensioned and shaped to provide a refractive power suitable for vision adapted to infinity with a refractive power adaptable to the dimensions of the eye in a range from minus 20 dioptre to plus 60 dioptre.

11. The kit according to claim 1,
wherein the capsule filing composition comprises cells capable of developing lens fibers and derived from one of an autologous human eye or a heterologous human eye or a non-human mammalian eye or a non-human, non-mammalian eye.

12. The kit according to claim 1,
wherein the capsule filling composition comprises one or more than one ingredients selected from the group consisting of:
hyaluronic acid,
an anti-TGFβ blocking agent,
a growth factor selected from the group consisting of a fibroblast growth factor,
epidermal growth factor (EGF), platelet-derived growth factor (PDGF), and
insulin growth factor I or II (IGF-I or IGF-II), and
a retinoid.

13. The kit according to claim 1,
wherein the lens implant is dimensioned to comprise a volume of at most 120 μl, 110 μl, 100 μl, 90 μl, 80 μl, 70 μl, 60 μl, 50 μl, 40 μl, 30 μl, 20 μl or 10 μl.

14. The kit according to claim 5,
wherein a radius of curvature of the posterior surface of the lens implant is in a range of 5 to 7 mm.

15. The kit according to claim 1,
wherein a maximal diameter of the implant measures at most 12, 11, 10, 9, 8, 7, 6 mm or 5 mm.

16. The kit according to claim 15,
wherein a maximal diameter of the implant measures at least 3, 4, 5, 6 or 7 mm.

17. The kit according to claim 8,
wherein the largest diameter of the opening measures in the range from 0.5 mm to less than 3 mm.

* * * * *